(12) United States Patent  
Farbos

(10) Patent No.: US 8,570,176 B2  
(45) Date of Patent: Oct. 29, 2013

(54) METHOD AND DEVICE FOR THE DETECTION OF MICROSLEEP EVENTS

(75) Inventor: Bruno Farbos, Montreal (CA)

(73) Assignee: 7352867 Canada Inc., Quebec (CA)

( * ) Notice: Subject to any disclaimer, the term of this patent is extended or adjusted under 35 U.S.C. 154(b) by 859 days.

(21) Appl. No.: 12/340,017

(22) Filed: Dec. 19, 2008

(65) Prior Publication Data

US 2009/0299209 A1    Dec. 3, 2009

Related U.S. Application Data

(60) Provisional application No. 61/071,966, filed on May 28, 2008.

(51) Int. Cl.  
*G08B 23/00*    (2006.01)

(52) U.S. Cl.  
USPC ........................................... 340/575

(58) Field of Classification Search  
USPC .......... 600/300, 301, 558; 340/575, 576, 143, 340/117, 206, 211, 573, 573.1; 348/77, 348/143; 250/336.1  
See application file for complete search history.

(56) References Cited

U.S. PATENT DOCUMENTS

| | | | |
|---|---|---|---|
| 3,863,243 A | 1/1975 | Skolnick et al. |
| 5,469,143 A | 11/1995 | Cooper |
| 5,570,698 A | 11/1996 | Liang et al. |
| 5,689,241 A | 11/1997 | Clarke, Sr. et al. |
| 5,729,619 A | 3/1998 | Puma |
| 5,786,765 A | 7/1998 | Kumakura et al. |
| 5,805,720 A | 9/1998 | Suenaga et al. |
| 5,878,156 A | 3/1999 | Okumura |
| 5,990,795 A | 11/1999 | Miller |
| 6,070,098 A | 5/2000 | Moore-Ede et al. |
| 6,087,941 A | 7/2000 | Ferraz |
| 6,097,295 A | 8/2000 | Griesinger et al. |
| 6,130,617 A | 10/2000 | Yeo |
| 6,154,559 A | 11/2000 | Beardsley |
| 6,218,947 B1 | 4/2001 | Sutherland |
| 6,243,015 B1 | 6/2001 | Yeo |
| 6,304,187 B1 | 10/2001 | Pirim |

(Continued)

FOREIGN PATENT DOCUMENTS

| | | |
|---|---|---|
| CA | 2 613 999 | 2/2007 |
| WO | WO 99/36893 | 7/1999 |

(Continued)

OTHER PUBLICATIONS

The International Search Report mailed Jul. 23, 2009, in corresponding PCT Patent Application No. PCT/CA2009/000732.

(Continued)

*Primary Examiner* — Brian Szmal  
(74) *Attorney, Agent, or Firm* — Edwards Wildman Palmer LLP; Mark D. Russett

(57) ABSTRACT

Disclosed herein is a method of detecting a microsleep event in a subject. The method includes determining a number of eye openness factors by measuring a number of distances between an upper eyelid and a lower eyelid of at least one eye over a time period. Graphical representations of the eye openness factors are then generated. Changes in the eye openness factors over the time period are correlated with a reference eye closure pattern indicative of the microsleep event. Also disclosed is a microsleep event detection device.

26 Claims, 6 Drawing Sheets

(56) References Cited

U.S. PATENT DOCUMENTS

| | | |
|---|---|---|
| 6,511,424 B1 | 1/2003 | Moore-Ede et al. |
| 6,542,081 B2 | 4/2003 | Torch |
| 6,717,518 B1 * | 4/2004 | Pirim et al. .................. 340/576 |
| 6,927,694 B1 | 8/2005 | Smith et al. |
| 6,974,326 B2 | 12/2005 | Marple-Horvat |
| 7,071,831 B2 | 7/2006 | Johns |
| 7,435,227 B2 | 10/2008 | Farbos |
| 2003/0151516 A1 | 8/2003 | Basir et al. |
| 2004/0090334 A1 | 5/2004 | Zhang et al. |
| 2007/0040691 A1 | 2/2007 | Lau et al. |

FOREIGN PATENT DOCUMENTS

| | | |
|---|---|---|
| WO | WO 03/012758 A1 | 2/2003 |
| WO | WO 2004/010365 A2 | 1/2004 |
| WO | WO 2006/092022 A1 | 9/2006 |

OTHER PUBLICATIONS

The Written Opinion mailed Jul. 23, 2009, in corresponding PCT Patent Application No. PCT/CA2009/000732.

* cited by examiner

METHOD AND DEVICE FOR THE DETECTION OF MICROSLEEP EVENTS

CROSS-REFERENCE TO RELATED APPLICATIONS

This application claims the benefit of previously filed U.S. Provisional Patent Application Ser. No. 61/071,966, filed on May 28, 2008, the contents of which are incorporated herein by reference.

TECHNICAL FIELD

The present invention concerns a method and device for the detection of microsleep events.

BACKGROUND

Methods for quantifying driving performance errors associated with sleep onset are of key importance for reducing the number of sleep related crashes. In the US, driver sleepiness is a major cause of motor vehicle crashes and is responsible for approximately 40,000 injuries and 1500 deaths each year. In one study, 55% of 1000 drivers surveyed indicated that they had driven while drowsy and 23% had fallen asleep at the wheel. This confirms other studies that sleepiness or sleep onset may play a role in vehicle crashes that are erroneously attributed to other causes.

Microsleep events are a useful indicator of sleep onset. A microsleep event often occurs as a result of sleep deprivation, or mental fatigue, sleep apnea, narcolepsy, or hypersomnia.

There are standardized methods for monitoring microsleep, which include: monitoring the electroencephalogram (EEG) and electrooculogram (EOG), video, test of performance, and the like. Of all these methods, the EEG is considered the most reliable for measuring sleepiness. However, both EEG and EOG, require the use of electrodes, which are attached to the subject, thereby making these methods inappropriate to routinely monitor any operators conducting fatigue prone tasks, such as, for example, vehicle drivers. The other methods are impractical because they are both difficult to set-up and because they require intensive data analysis by humans thereby making data treatment difficult to automate.

There are various ways by which microsleep episodes can be identified. Some experts define microsleep according to behavioral criteria (eyelids closure), while others rely on electroencephalogram markers such as a 3-15 second episode (shorter durations would be difficult to visually detect and longer times would qualify as sleep onset.) during which 4-7 Hz (theta wave) activity replaced the waking 14-20 Hz (alpha wave) background rhythm.

Microsleep, subjectively related to the sensation of "nodding off", is associated with the interruption of the blinking artifacts characteristic of full wakefulness. During microsleep events, attention lapses can impair the ability to detect and respond to crucial stimuli and events. For example, microsleeps (or microsleep episodes) can become extremely dangerous when occurring during situations which require continual alertness, such as driving a motor vehicle or operating machinery. People who experience microsleeps usually remain unaware of them, instead believing themselves to have been awake the whole time, or feeling a sensation of 'spacing out'. The sleepy driver is at very high risk of having an accident during a microsleep episode. Many accidents have occurred because of microsleep episodes.

Clearly, the ability to detect microsleep events would be useful as a means of alerting and warning drowsy drivers of such events.

Several studies have used "quantitative" EEG methods to identify driver sleepiness. Theta power (EEG waves), and the frequency of theta bursts typically increase during prolonged driving, and are associated with poor driving performance. Disadvantageously, these techniques typically average EEG activity over several seconds (up to 1 minute), and therefore could not be used to detect brief microsleep events of between 3 seconds and 15 seconds.

A variety of physiological measures have been proposed to alert drivers to the onset of drowsiness.

One of the most investigated is PERCLOS (or PERcent CLOSure), which measures drowsiness as the percent of time a driver's eyes are closed over a time period. When a sufficient number of open/closed patterns are obtained, PERCLOS will trigger an alarm. PERCLOS works at percentages greater than 80%, which typically means that within 1 minute, the eyes of the individual must be closed for 48 seconds before an alarm is triggered. Clearly, this delay in unacceptable in tasks such as driving a vehicle because by the time PERCLOS activates the alarm, the driver will already have either fallen asleep, or be on the verge of falling asleep. Therefore, disadvantageously PERCLOS is too slow a system to allow preventive actions to be taken before an individual, such as a driver, experiences the first signs of sleepiness.

EOG records, which are made to exclude potential artifacts during EEG records, also show that normal eye blinks often continue during microsleep events, indicating that the eyes are at least partially open.

Another physiological measure, which is based on measurements of eye closure and which supposedly alerts drivers to the onset of drowsiness, is the measurement of peak blink velocities, as described in U.S. Pat. No. 7,071,831B2. The system described therein includes a pair of glasses or spectacle frames that must be worn by the individuals in order to monitor the occurrence of eye blinks. However, this kind of device must be carried or worn by operators (i.e. portable devices).

Thus, there is a need for a detection method and device for the detection of microsleep events in a subject as an indicator of sleep onset that is able to detect brief microsleep events, at early stages, not requiring the use of electrodes or other portable devices.

SUMMARY

We have unexpectedly discovered that microsleep events can be easily and readily detected by measuring the closing and opening patterns of the eyelids over time using a microsleep detection process, converting the raw data collected from the measurements into graphs and comparing the graphs to those of stored, standardized microsleep patterns.

Accordingly, in one aspect there is provided a method of detecting a microsleep event in a subject, the method comprising:—determining a plurality of eye openness factors by measuring a plurality of distances between an upper eyelid and a lower eyelid of at least one eye over a time period;—generating graphical representations of the eye openness factors; and—correlating changes in the eye openness factors over the time period with a reference eye closure pattern indicative of the microsleep event.

The method, as described above, further comprising: illuminating the face of the subject; and recording a facial image. A digital camera having an infra-red source is used to illuminate the face and to record the facial image.

The method, as described above, further comprising: identifying the eye and the eyelids by using a facial feature recognition algorithm.

The method, as described above, further comprising: verifying the presence of microsleep characteristic eye openness factor levels by measuring the eye openness factors as a function of time for a blink cycle of the eye. The eye openness factors levels include at least one eye openness level. The eye openness factors include one or more eye openness levels and five or less eye openness levels. The eye openness factors include five eye openness levels. The eye openness levels are associated with an open eye, the closure of the eyelids, partial or closed eye, and opening of the eyelids.

The method, as described above, in which the eye openness factors include five successive eye openness levels, the sequential detection of the five levels being indicative of microsleep characteristics. The method further comprising: determining additional eye openness factors if less than five successive eye openness factor levels are detected.

The method, as described above, further comprising: computing eye opening and eye closure representative curves. The eye closure representative curves are computed using a negative slope and a second order polynomial regression applied to the eye openness factors of the first and second eye openness factor levels. The eye opening factors are computed using a positive slope and a second order polynomial regression applied to the eye openness factors of the fourth and fifth eye openness factor levels. The method further comprising: verifying the presence of microsleep eye opening and closing representative curves by computing the Pearson coefficient of the eye closure representative curves with regard to the first and second eye openness factor levels and the eye opening representative curves with regard to the fourth and fifth eye factor levels. The subject is informed when the Pearson coefficients are greater than or equal to a predetermined threshold value.

The method, as described above, in which images of the face are sampled at a frequency of between 10 Hz and 60 Hz.

The method, as described above, further comprising: a sub-process for detecting microsleep characteristic eye openness factor levels at an image sampling frequency of 20 Hz. The sub-process comprises: verifying that a first level is detected by confirming the presence of a series six or more successive eye openness factors corresponding to an open eye.

The method, as described above, further comprising: verifying that a second level is detected by confirming the presence of a series four or more successive decreasing eye openness factors. The method, as described above, further comprising: verifying that a third level is detected by confirming the presence of a series of a minimum of five and a maximum of one-hundred and twenty successive eye openness factors.

The method, as described above, further comprising: verifying that a fourth level is detected by confirming the presence of a series of a minimum of four successive eye openness factors.

The method, as described above, further comprising: verifying that a fifth level is detected by confirming the presence of a series of a minimum of six successive eye openness factors corresponding to the open eye.

The method, as described above, further comprising: alerting the subject to the presence of the microsleep event.

According to another aspect, there is provided a microsleep event detection device, the device comprising:

a facial image sampler for sampling facial images over time of a subject, the sampler having an infra red source for illuminating one or more eyes of the subject;

a microprocessor having electronically stored therein an electronically executable microsleep detection process, the microprocessor being connected to the sampler for receiving the sampled facial images, the images being electronically converted to graphical representations of eye openness factors; and a memory associated with the microprocessor, the memory having stored therein a plurality of reference eye closure patterns for electronically correlating the eye openness factors with the reference eye closure patterns.

The device, as described above further comprises an alert connected to the microprocessor for alerting the subject to the microsleep event.

Accordingly, in another aspect there is provided a method of alerting a vehicle operator to a microsleep event, the method comprising:

determining a plurality of eye openness factors by measuring a plurality of distances between an upper eyelid and a lower eyelid of at least one eye over a time period;

generating graphical representations of the eye openness factors;

correlating changes in the eye openness factors over the time period with a reference eye closure pattern indicative of the microsleep event; and triggering an alarm so as to alert the operator to the microsleep event.

Accordingly, in yet another aspect, there is provided a method of correlating EEG and EOG microsleep patterns with eye closure patterns, the method comprising:

measuring EEG and EOG microsleep patterns in a subject;

determining a plurality of eye openness factors by measuring a plurality of distances between an upper eyelid and a lower eyelid of at least one eye over a time period;

generating graphical representations of the eye openness factors; and correlating changes in the eye openness factors with the EEG and EOG microsleep patterns.

BRIEF DESCRIPTION OF THE FIGURES

Embodiments of the invention will be described by way of example only with reference to the accompany drawings, in which.

DETAILED DESCRIPTION

Generally stated, the non-limitative illustrative embodiment of the present invention provides a method and device for the detection of microsleep events in a human subject based on the analysis of eye closure patterns of at least one eye, typically both eyes, which occur during microsleep events.

During microsleep events, measured by EEG and EOG, we observed a progressive variation of the distance between an upper eyelid and a lower eyelid of a human subject over time. We now describe hereinbelow a method and device, which provides complementary evidence of impending sleep in drowsy operators, such as vehicle drivers, airplane pilots, air traffic controllers and the like, using eye closure patterns, which when detected, alerts sleepy operators to unsafe situations before eyelid closure occurs, thereby correlating EEG and EOG microsleep patterns with eye closure patterns.

Also described is a method for the analysis of eye closure patterns allowing the differentiation between a normal eyelid closure and one due to drowsiness.

Figure 1:
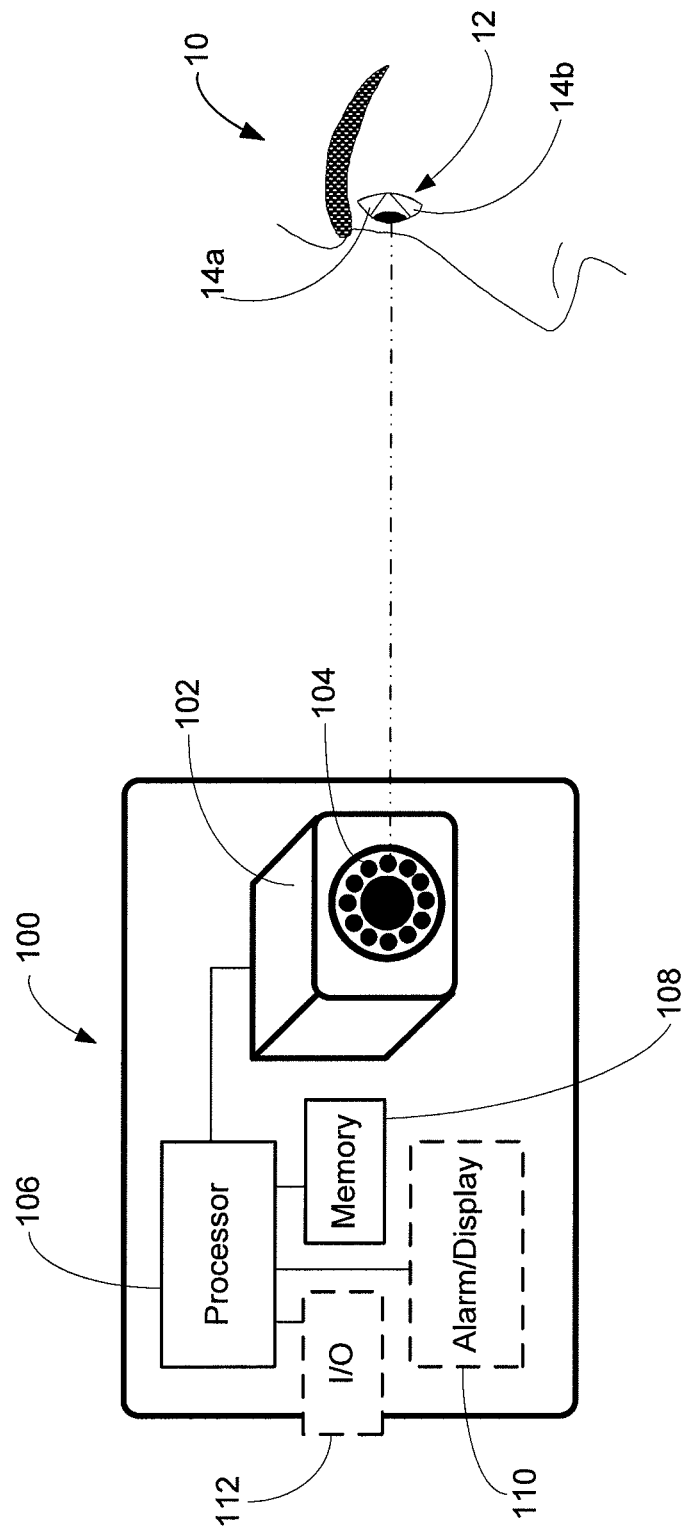
FIG. 1 is a block diagram of a microsleep detection device according to an illustrative embodiment of the present invention, the device being used on a subject.

Referring to FIG. 1, there is shown an example of a microsleep event detection device 100, which generally comprises facial image sampler such as a digital camera 102 with an associated infrared source 104, a microprocessor 106 with an associated memory 108 and either or both an alarm/display 110 and input/output interface 112.

Thus, in one example, there is described a method using the device 100 for detecting a microsleep event in a human subject. The method comprises: determining a plurality of eye openness factors by measuring a plurality of distances between an upper eyelid and a lower eyelid of at least one eye, typically both eyes, over a time period; generating graphical representations of the eye openness factors; and correlating changes in the eye openness factors over the time period with a reference eye closure pattern indicative of the microsleep event.

In operation, the digital camera 102 is aimed at the face of a subject 10 and illuminates his or her eyes 12 using the infrared source 104 in order to determine the eye openness factor, i.e. a value representative of the distance between the upper 14a and lower 14b eyelids. The images taken by the digital camera 102 are then processed by the processor 106 which executes a microsleep event detection process stored on its associated memory 108. Upon detection of a microsleep event, the microsleep event detection device 100 may inform the user of a microsleep event by triggering an integrated alarm and/or display 110 or provide the information to a further process or device via the input/output interface 112. It is to be understood that other components may be added to the microsleep event detection device 100 such as, for example, a user interface and a wireless communication device.

Figure 2:
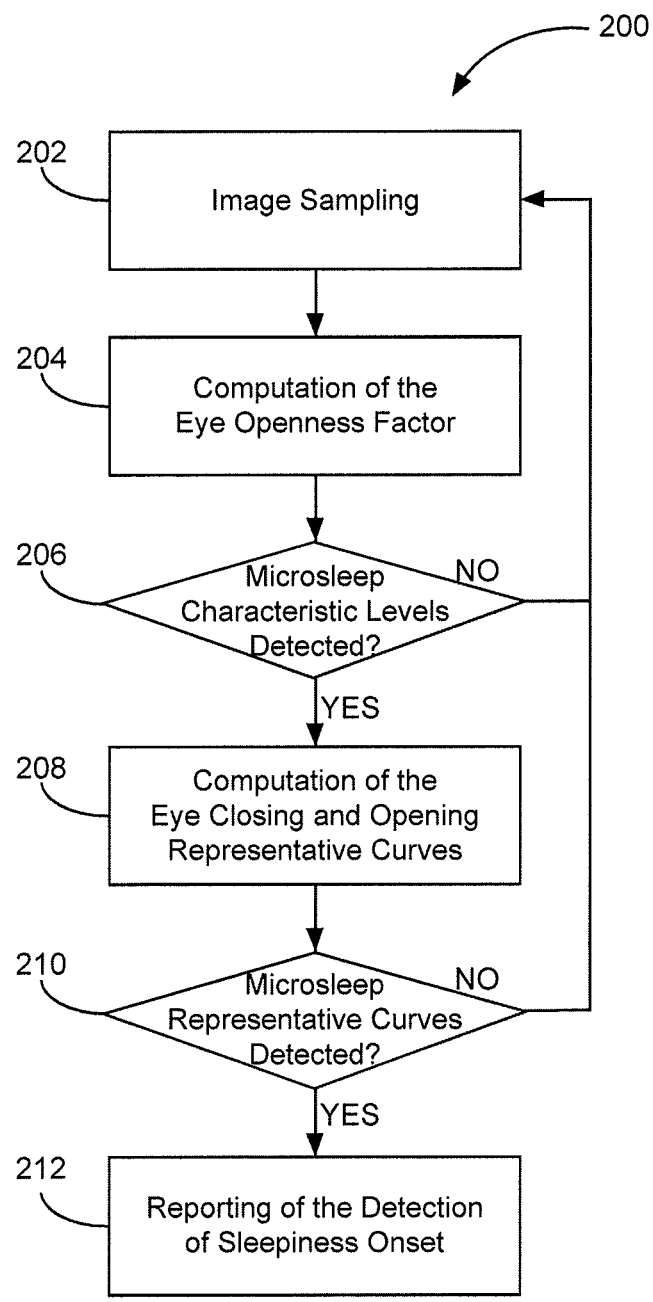
FIG. 2 is a flow diagram of a microsleep event detection process that may be used by the device of FIG. 1.

Referring now to FIG. 2, there is shown a flow diagram of a microsleep event detection process 200 that may be electronically executed by the processor 106 of the microsleep event detection device 100 of FIG. 1. The steps of the process 200 are indicated by blocks 202 to 212. The process 200 starts at block 202 by sampling an image of the face of a subject 10 using the digital camera 102. The digital camera 102 may sample images at a frequency between about 10 and 60 Hz (i.e. sampling frequency). At block 204, the process 200 identifies, in the sampled digital image, the eye 12 and eyelids 14a, 14b of the subject 10. This may be accomplished using a facial feature recognition algorithm executed by the processor 106. Then, the eye openness factor is computed.

Figure 3A:
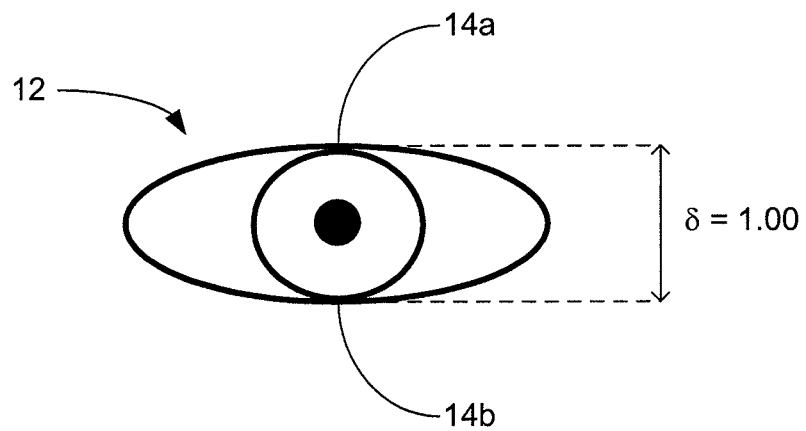
FIGS. 3A and 3B are schematic views of the fully open eye (FIG. 3A) and the fully closed eye (FIG. 3B) with their associated eye openness factor.
Figure 3B:
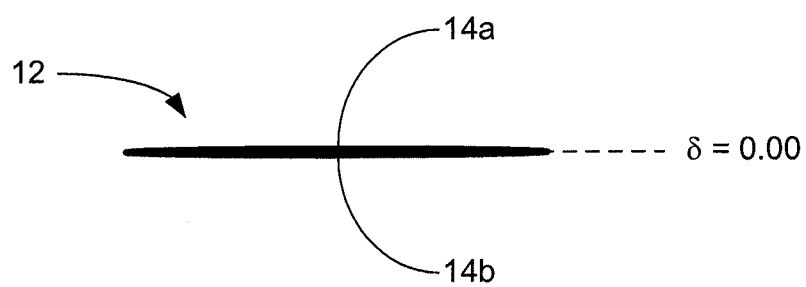

Referring now to FIGS. 3A and 3B, the eye openness factor may be expressed as δ having a value between 1, representing a fully open eye 12 (see FIG. 3A), and 0, representing a fully closed eye 12 (see FIG. 3B). The value of δ may be computed, for example, by dividing the measured distance between the upper 14a and lower 14b eyelids positions in a Cartesian representation (X,Y) by a reference measure of the fully open eye D. Thus:

$$\delta = (\text{upper lid position}(x_u, y_u) - \text{lower lid position}(x_l, y_l))/D,$$

where D=upper lid position $(x_U, y_U)$–lower lid position $(x_L, y_L)$ and $(x_u, y_u)$=instant upper lid position, $(x_l, y_l)$=instant lower lid position, $(x_U, y_U)$=upper lid position at maximum eye opening and $(x_L, y_L)$=lower lid position at maximum eye opening.

Referring again to FIG. 2 at block 206, the process verifies if the microsleep characteristic eye openness factor levels are present.

Figure 4:
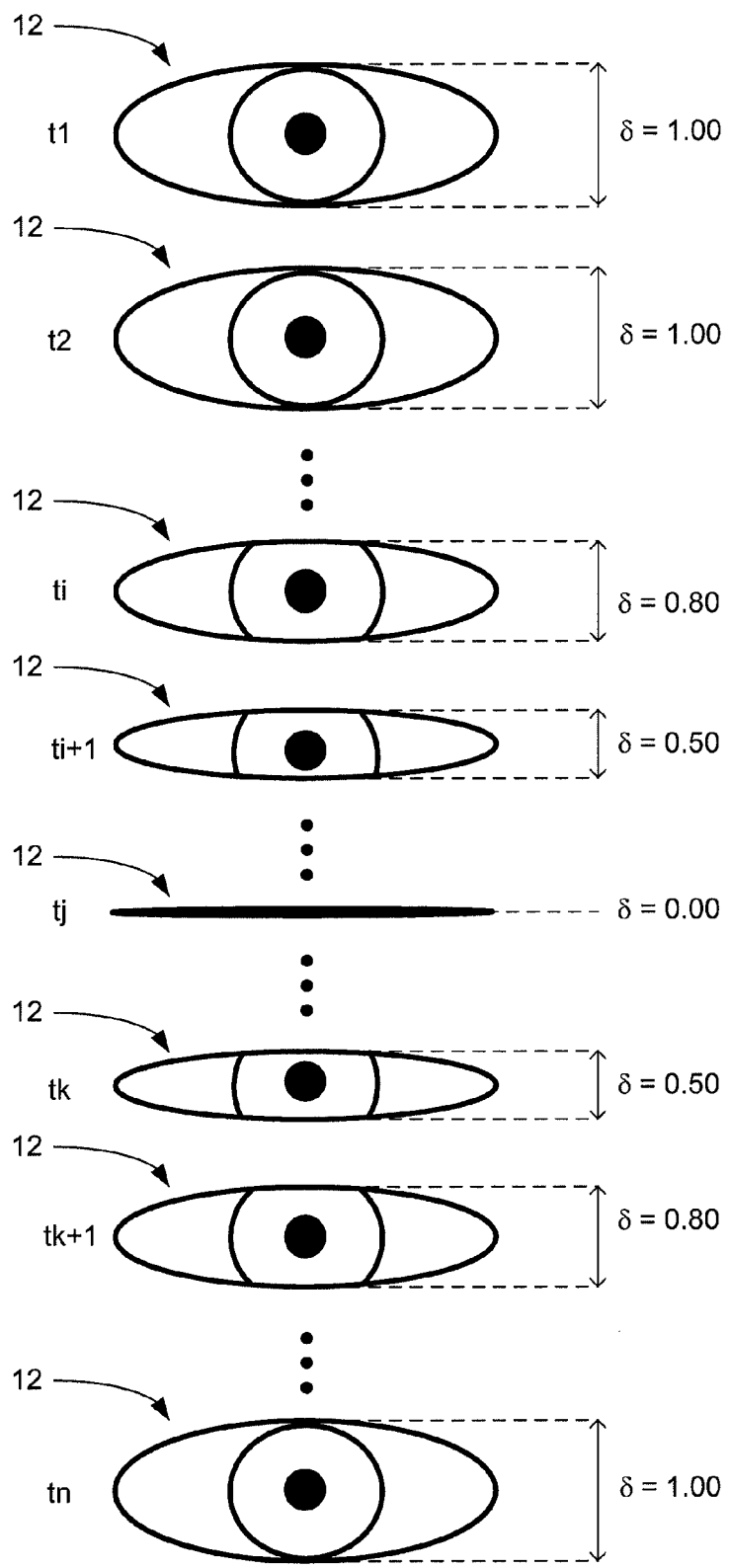
FIG. 4 is a series of schematic views of an example of the variation of the eye openness factor as a function of time for a blink cycle.

Referring to FIG. 4, there is shown an illustrative example of the variation of the eye openness factor as a function of time for a blink cycle. The blink cycle starts at time $t_1$ with a fully open eye 12 (eye openness factor δ=1.00), at $t_2$ the eye openness factor remains at δ=1.00, then decreases, going through δ=0.80 and δ=0.50 at times $t_i$ and $t_{i+1}$, until it reaches δ=0.00 at time $t_j$ (fully closed eye 12), and then increases, going through δ=0.50 and δ=0.80 at times $t_k$ and $t_{k+1}$, until it reaches δ=1.00 again at $t_n$. It is to be understood that the blink cycle illustrated in FIG. 4 for illustrative purpose only and that an actual cycle would comprise a number of sample times depending the sample frequency.

Figure 5:
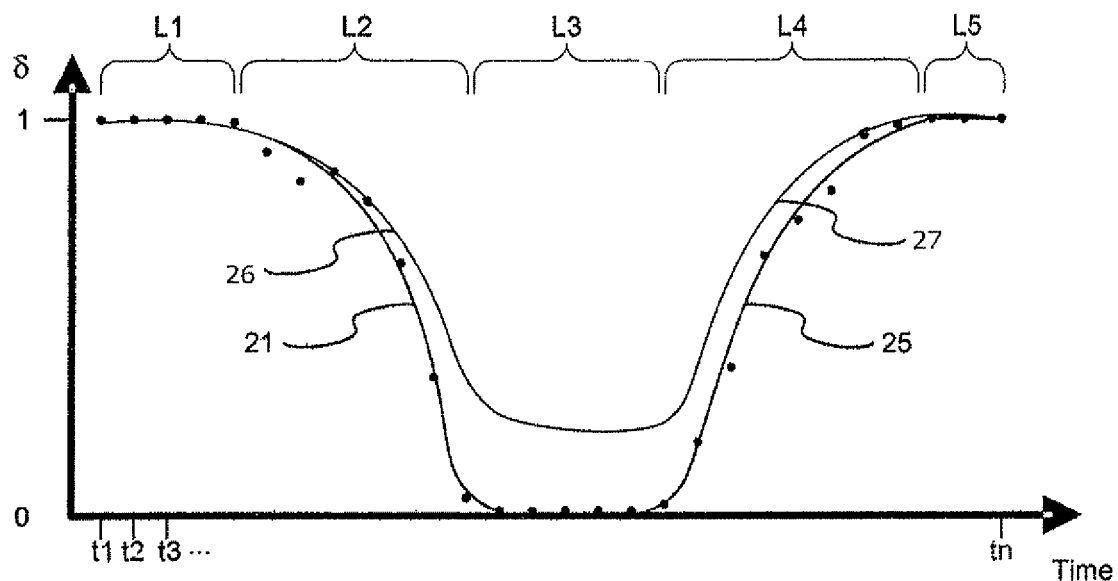
FIG. 5 is an illustrative example of the fully closed eye (period L4 and L5), at the moment of a microsleep.

Referring now to FIG. 5, these computed eye openness factors, as a function of time, can be represented in a graph which may be generally characterized by five successive levels, L1 to L5. The first and last levels, L1 and L5, are associated with the open eye (i.e. δ=1.00), the second level, L2, with the closure of the eyelids, 14a, 14b (i.e. 0.00>δ>0.00, δ decreasing), the third level L3, with the partial or closed eye (i.e. 0.00<δ<0.5 for example) and fourth level, L4, with the opening of the eyelids 14a, 14b (i.e. 0.00<δ<1.00, δ increasing).

Referring again to FIG. 2, the process 200 detects all five levels, i.e. L1 to L5, it then proceeds to block 208. If not, it proceeds back to block 202 for the next image sample. At block 208, the process computes the eye closure 21 or 26 and eye opening 25 or 27 representative curves. The eye closure representative curve 21 or 26 is computed using negative slope second order polynomial regression (parabolic curve), i.e.

$$Y = d_0 + d_1 \cdot X + d_2 \cdot X^2.$$

where Y is the predicted outcome value for the polynomial model with regression coefficients $d_1$ to $_2$ for each degree and Y intercept d1; which is applied to the eye openness factors composing the first and second eye openness factor levels, i.e. L1 and L2. As for the eye opening representative curve 25 or 27, it is computed using positive slope second order polynomial regression applied to the eye openness factors composing the fourth and fifth eye openness factor levels, i.e. L4 and L5. Then, at block 210, the process 220 verifies if the microsleep eye opening and closing representative curves are present. This is accomplished by computing the Pearson coefficient, r:

$$r = \frac{\sum XY - \frac{\sum X \sum Y}{N}}{\sqrt{\left(\sum X^2 - \frac{(\sum X)^2}{N}\right)\left(\sum Y^2 - \frac{(\sum Y)^2}{N}\right)}}$$

where X and Y are positions in a Cartesian representation; of the eye closure representative curve 21 or 26 with regard to the eye openness factors composing eye openness factor levels L1 and L2, and of the eye opening representative curve 25 or 27 with regard to the eye openness factors composing the eye openness factor levels L4 and L5. If both Pearson coefficients are greater or equal to a given threshold such as, for example, 0.9, then the process 200 proceeds to block 212. If not, it proceeds back to block 202 for next image sample. Finally, at block 212, the microsleep event detection device 100 may inform the user 10 of the detection of a microsleep event state via the integrated alarm and/or display 110 or provide the information to a further process or device via the input/output interface 112 (see FIG. 1) using, for instance, a wired or wireless telecommunication link such as, for example, Bluetooth, WiFi and the like.

It is to be understood that the Pearson coefficient threshold is not meant to be restricted to 0.9 and may be adjusted to suit a desired confidence level. It may also vary depending on the resolution of the digital camera 102 (see FIG. 1).

The eye closure pattern is based on these particular observations closing, duration of the eyelid complete or partial closure and re-opening. More precisely, the eye closure pattern indicates a progressive decreasing followed by a baseline period where the eyelids are fully closed and then a reopening. If all the above occur, then a microsleep is detected.

Figure 6:
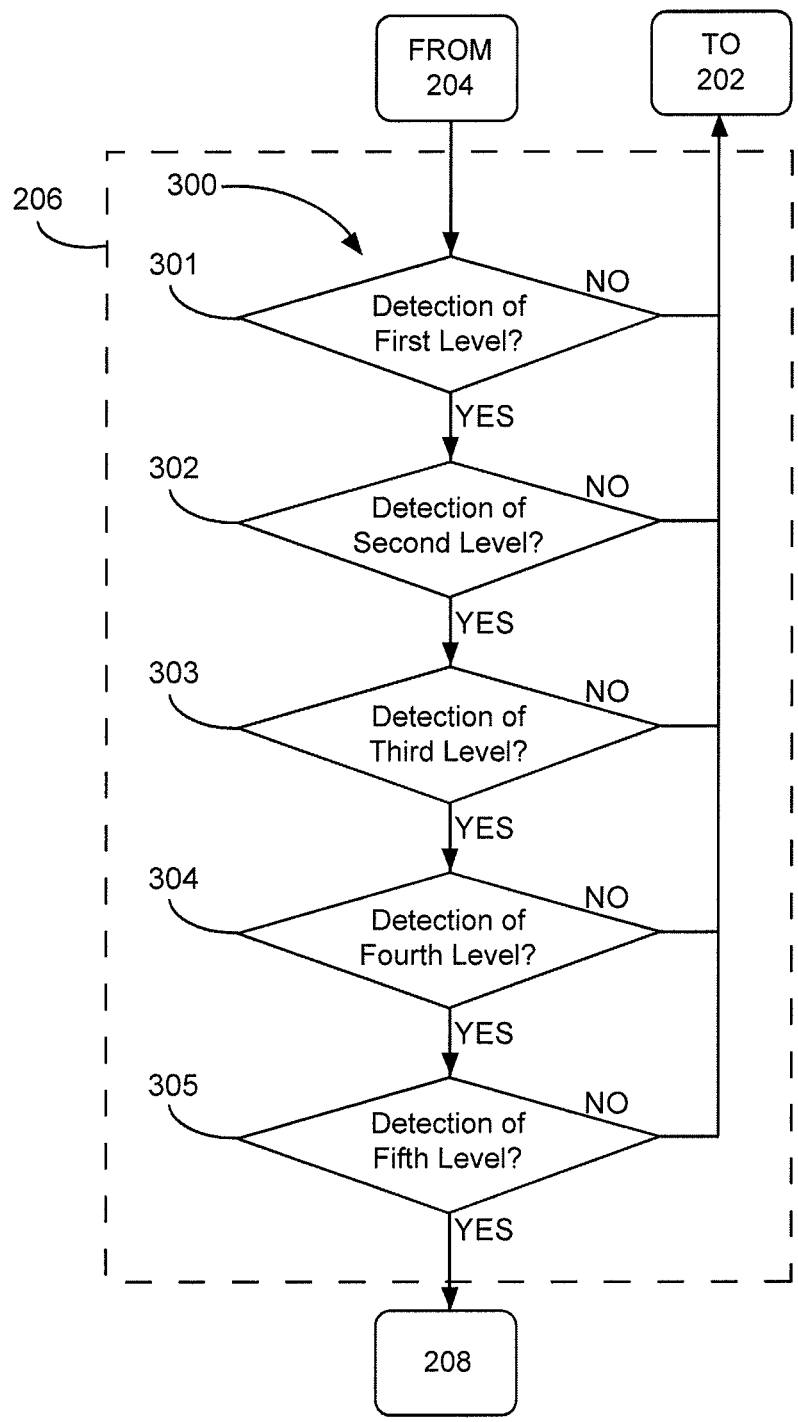
FIG. 6 is a flow diagram of a microsleep characteristic eye openness factor levels detection sub-process that may be used with the microsleep event detection process of FIG. 2 for an image sampling frequency of 20 Hz.

Example of Microsleep Characteristic Eye Openness Factor Levels at an Image Sampling Frequency of 20 GHz Referring now to FIG. 6, there is shown a flow diagram a microsleep characteristic eye openness factor levels detection sub-process 300 that may be executed at block 206 of process 200 in order to detect the presence of the five microsleep characteristic eye openness factor levels, i.e. L1 to L5 (see FIG. 5) for an image sampling frequency of 20 Hz. The steps of the sub-process 300 are indicated by blocks 301 to 305.

At block 301, the sub-process 300 verifies if the first level L1 is detected. To that end, the sub-process 300 checks if a series of a minimum of six (6) successive eye openness factors having a value of $\delta=1.00$ is present. If so, the sub-process 300 proceeds to block 302, if not, it goes back to block 202 of process 200 (see FIG. 2).

At block 302, the sub-process 300 verifies if the second level L2 is detected. To that end, the sub-process 300 checks if a series of a minimum of four (4) successive decreasing eye openness factors having values between of $\delta=0.99$ and $\delta=0.01$ is present. If so, the sub-process 300 proceeds to block 303, if not, it goes back to block 202 of process 200 (see FIG. 2).

Then, at block 303, the sub-process 300 verifies if the third level L3 is detected. To that end, the sub-process 300 checks if a series of a minimum of five (5) and a maximum of 120 successive eye openness factors having a value of $\delta=0.00$ is present. If so, the sub-process 300 proceeds to block 304, if not, it goes back to block 202 of process 200 (see FIG. 2).

At block 304, the sub-process 300 verifies if the fourth level L4 is detected. To that end, the sub-process 300 checks if a series of a minimum of four (4) successive increasing eye openness factors having values between of $\delta=0.01$ and $\delta=0.99$ is present. If so, the sub-process 300 proceeds to block 305, if not, it goes back to block 202 of process 200 (see FIG. 2).

Finally, at block 305, the sub-process 300 verifies if the fifth level L5 is detected. To that end, the sub-process 300 checks if a series of a minimum of six (6) successive eye openness factors having a value of $\delta=1.00$ is present. If so, the sub-process 300 proceeds to block 208 of process 200 (see FIG. 2), the presence of all five (5) microsleep characteristic eye openness factor levels. If not, the sub-process 300 goes back to block 202 of process 200 (see FIG. 2). It is to be understood that the number of eye openness factors used to detect the presence of each microsleep characteristic eye openness factor level may vary, for example according to the image sampling frequency and are meant as illustrative examples only.

It is to be understood that the memory associated with the microprocessor as described above, contains a plurality of reference eye closure patterns stored therein. The graphs as illustrated in FIG. 5 are compared to the reference eye closure patterns. Once a match is found, a microsleep event is verified and the alarm is activated Although the present invention has been described by way of a particular embodiment and examples thereof, it should be noted that it will be apparent to persons skilled in the art that modifications may be applied to the present particular embodiment without departing from the scope of the present invention.

What is claimed is:

1. A method of alerting a vehicle operator to a microsleep event, the method comprising:
    determining a plurality of eye openness factors by measuring a plurality of distances between an upper eyelid and a lower eyelid of at least one eye over a time period;
    generating graphical representations of the eye openness factors; and
    correlating changes in the eye openness factors over the time period with a reference eye closure pattern indicative of the microsleep event; and
    triggering an alarm so as to alert the operator when the eye openness factors, compared to a reference eye closure pattern, are indicative of the microsleep event.

2. The method, according to claim 1, further comprising: illuminating the face of the vehicle operator; and recording a facial image.

3. The method, according to claim 2, in which a digital camera having an infra-red source is used to illuminate the face and to record the facial image.

4. The method, according to claim 3, in which images of the face are sampled at a frequency of between 10 Hz and 60 Hz.

5. The method, according to claim 1, further comprising: verifying the presence of microsleep characteristic eye openness factor levels by measuring the eye openness factors as a function of time for a blink cycle of the eye.

6. The method, according to claim 5, in which the eye openness factors levels include at least one eye openness level.

7. The method, according to claim 5, in which the eye openness factors include one to five eye openness levels.

8. The method, according to claim 5, in which the eye openness factors include five eye openness levels.

9. The method, according to claim 5, in which the eye openness levels are associated with an open eye, the closure of the eyelids, partial or closed eye, and opening of the eyelids.

10. The method, according to claim 5, further comprising: a sub-process for detecting microsleep characteristic eye openness factor levels at an image sampling frequency of 20 Hz.

11. The method, according to claim 10, in which the sub-process comprises: verifying that a first level is detected by confirming the presence of a series six or more successive eye openness factors corresponding to an open eye.

12. The method, according to claim 11, further comprising: verifying that a second level is detected by confirming the presence of a series four or more successive decreasing eye openness factors.

13. The method, according to claim 12, further comprising: verifying that a third level is detected by confirming the presence of a series of a minimum of five and a maximum of one-hundred and twenty successive eye openness factors.

14. The method, according to claim 13, further comprising: verifying that a fourth level is detected by confirming the presence of a series of at least four successive eye openness factors.

15. The method, according to claim 14, further comprising: verifying that a fifth level is detected by confirming the presence of a series of a minimum of six successive eye openness factors corresponding to the open eye.

16. The method, according to claim 1, in which the eye openness factors include five successive eye openness levels, the sequential detection of the five levels being indicative of microsleep characteristics.

17. The method, according to claim 16, further comprising: determining additional eye openness factors if less than five successive eye openness levels are detected.

18. The method, according to claim 5, further comprising: computing eye opening and eye closure representative curves.

19. The method, according to claim 18, in which the eye closure representative curves are computed using a negative slope and a second order polynomial regression applied to the eye openness factors of first and second eye openness factor levels.

20. The method, according to claim 18, in which the eye opening factors are computed using a positive slope and a second order polynomial regression applied to the eye openness factors of fourth and fifth eye openness factor levels.

21. The method, according to claim 18, further comprising: verifying the presence of microsleep eye opening and closing representative curves by computing the Pearson coefficient of the eye closure representative curves with regard to first and second eye openness factor levels and the eye opening representative curves with regard to fourth and fifth eye openness factor levels.

22. The method, according to claim 21, in which the vehicle operator is informed when the Pearson coefficients are greater than or equal to a predetermined threshold value.

23. The method, according to claim 1, further comprising: alerting the vehicle operator to the presence of the microsleep event.

24. A microsleep event detection device, the device comprising:
   a facial image sampler for sampling facial images over time of a subject, the sampler having an infra red source for illuminating one or more eyes of the subject and for measuring the distance between upper eyelids and lower eyelids of the subject;
   a microprocessor connected to the sampler for receiving the sampled facial images, and for converting the sampled facial images to graphical representations of eye openness factors;
   a non-transitory memory electronically connected to the microprocessor, the memory having stored therein a plurality of reference eye closure patterns; and
   an alarm connected to the microprocessor for alerting the subject when the eye openness factors, compared to a reference eye closure pattern, are indicative of the microsleep event.

25. The device, according to claim 24, further comprising an alert connected to the microprocessor for alerting the subject to the microsleep event.

26. A computer-implemented method of detecting a microsleep event in a subject, the method comprising:
   receiving a signal from an infra red source at one or more eyes of the subject;
   determining a plurality of eye openness factors by measuring a plurality of distances between an upper eyelid and a lower eyelid of at least one eye over a time period;
   generating graphical representations of the eye openness factors; and
   triggering an alarm to alert the subject when the eye openness factors, compared to a reference eye closure pattern, are indicative of the microsleep event.

* * * * *